(12) United States Patent
Umebayashi et al.

(10) Patent No.: US 7,740,732 B2
(45) Date of Patent: Jun. 22, 2010

(54) METHOD FOR PRODUCING DISPOSABLE WORN ARTICLE

(75) Inventors: Toyoshi Umebayashi, Osaka (JP); Masaki Nakakado, Osaka (JP)

(73) Assignee: Zuiko Corporation, Osaka (JP)

( * ) Notice: Subject to any disclaimer, the term of this patent is extended or adjusted under 35 U.S.C. 154(b) by 404 days.

(21) Appl. No.: 11/721,816

(22) PCT Filed: Dec. 19, 2005

(86) PCT No.: PCT/JP2005/023248
§ 371 (c)(1),
(2), (4) Date: Jun. 15, 2007

(87) PCT Pub. No.: WO2006/068081
PCT Pub. Date: Jun. 29, 2006

(65) Prior Publication Data
US 2008/0099130 A1     May 1, 2008

(30) Foreign Application Priority Data
Dec. 24, 2004   (JP) .............................. 2004-372952
Apr. 6, 2005    (JP) .............................. 2005-109684

(51) Int. Cl.
*B29C 65/00*   (2006.01)
*B32B 37/00*   (2006.01)
*B32B 38/04*   (2006.01)
*H05K 13/04*   (2006.01)
*E04F 13/08*   (2006.01)
*A61F 13/15*   (2006.01)
*A61F 13/20*   (2006.01)

(52) U.S. Cl. ................. 156/302; 156/269; 156/271; 156/297; 156/299; 604/385.01; 604/385.21

(58) Field of Classification Search .............. 156/60, 156/196, 199, 200, 204, 221, 226, 250, 252, 156/253, 267, 269, 297, 299, 300, 301, 302, 156/303, 443, 459, 461, 464, 510, 516, 522, 156/538, 539, 543, 552, 556, 559, 566, 578, 156/271; 604/358, 367, 374, 378, 383, 385.01, 604/385.03, 385.09, 385.201, 385.21, 385.22, 604/385.23
See application file for complete search history.

(56) References Cited

U.S. PATENT DOCUMENTS

2001/0042584 A1* 11/2001 Karami et al. ................. 156/66
(Continued)

FOREIGN PATENT DOCUMENTS

JP          03-176053         7/1991
(Continued)

OTHER PUBLICATIONS

International Search Report for corresponding Application No. PCT/JP2005/023248 mailed Jan. 17, 2006.

*Primary Examiner*—Richard Crispino
*Assistant Examiner*—Brian R Slawski
(74) *Attorney, Agent, or Firm*—Renner, Otto, Boisselle & Sklar, LLP

(57) ABSTRACT

A method for producing a disposable worn article of the present invention is directed to a method for producing a worn article including a core portion 2 covering the crotch of the wearer, and a torso portion 3 that fits to the torso of the wearer, wherein the torso portion 3 includes a back portion 3L and a front portion 3S. The method includes: a step of carrying a first web W1 including a waist portion 31 of a first back portion 3L1 and a second web W2 including a waist portion 31 of a second back portion 3L2 in the longitudinal direction Y of the webs; a step of forming a combined member by placing the core portion 2 so as to bridge between the first and second webs W1 and W2; and a step of cutting the combined member so as to divide the combined member into a first group G1 and a second group G2.

6 Claims, 13 Drawing Sheets

U.S. PATENT DOCUMENTS

| | | |
|---|---|---|
| 2002/0112276 A1* | 8/2002 | Ruman et al. .................... 2/400 |
| 2002/0129888 A1* | 9/2002 | Otsubo et al. ................ 156/161 |
| 2003/0135192 A1* | 7/2003 | Guralski et al. ............. 604/391 |
| 2003/0168159 A1* | 9/2003 | Een et al. ..................... 156/264 |
| 2004/0035521 A1 | 2/2004 | Nakakado et al. |
| 2006/0196594 A1 | 9/2006 | Shimizu et al. |

FOREIGN PATENT DOCUMENTS

| | | |
|---|---|---|
| JP | 03-195555 | 8/1991 |
| JP | 09066071 A * | 3/1997 |
| JP | 2003/102777 | 4/2003 |
| JP | 2003-175066 | 6/2003 |
| JP | 2004-223238 | 8/2004 |
| JP | 2004-329590 | 11/2004 |
| JP | 2005-522272 | 7/2005 |
| WO | 03/086258 | 10/2003 |
| WO | 2004/085300 | 10/2004 |

* cited by examiner

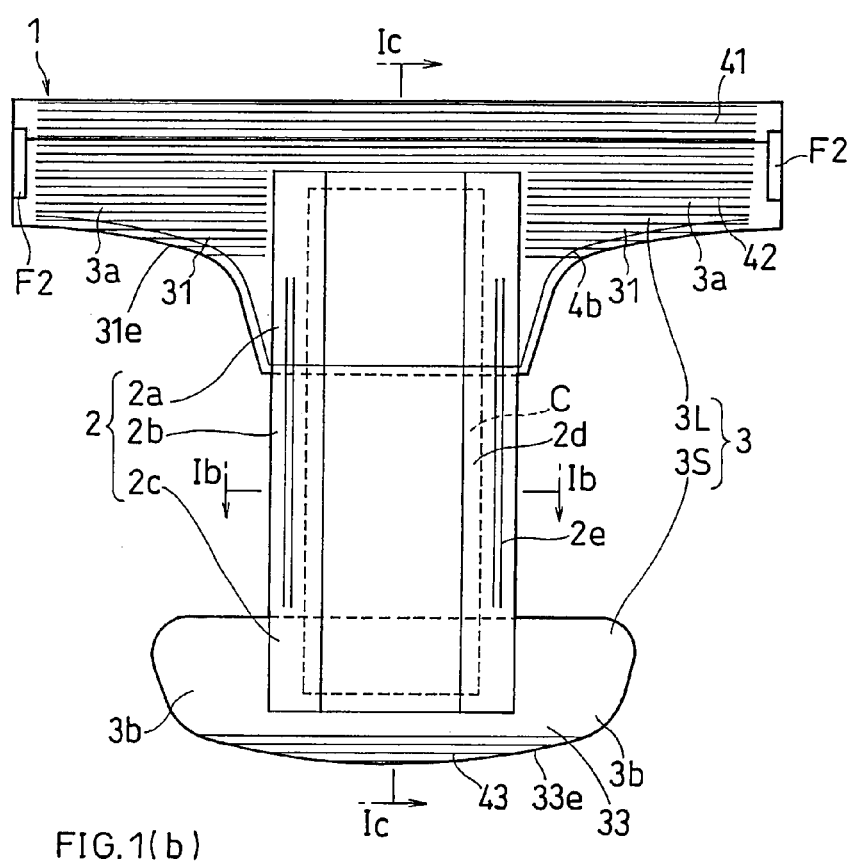
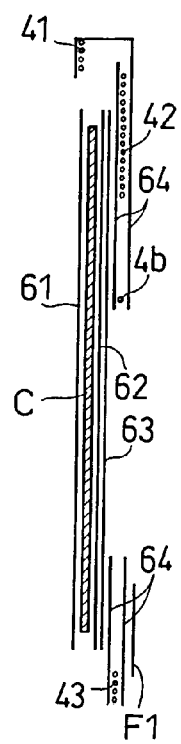
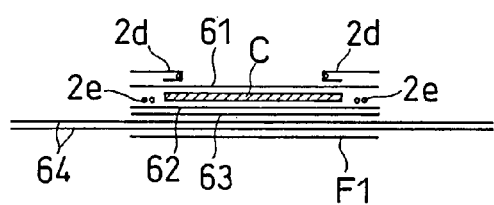

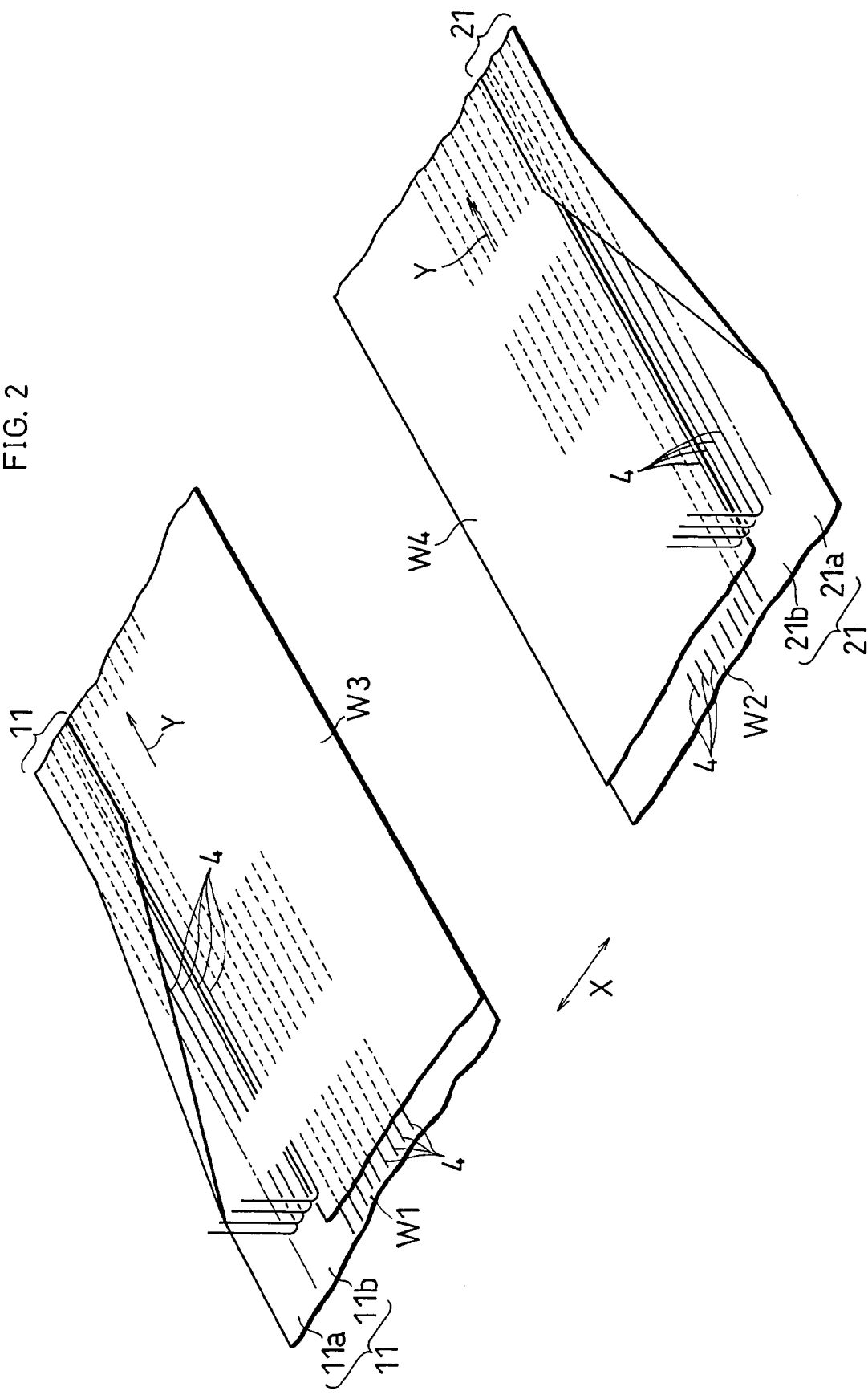

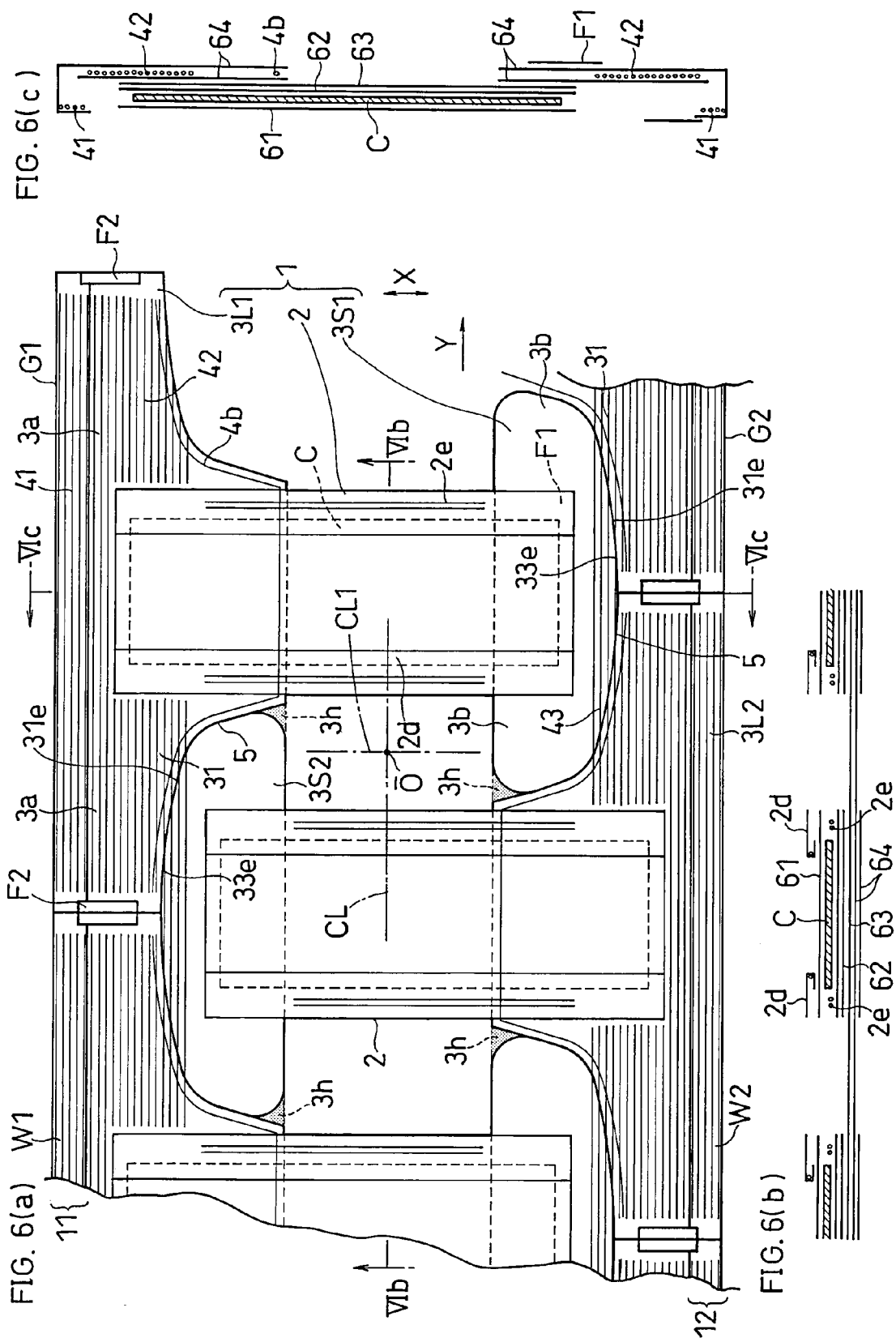

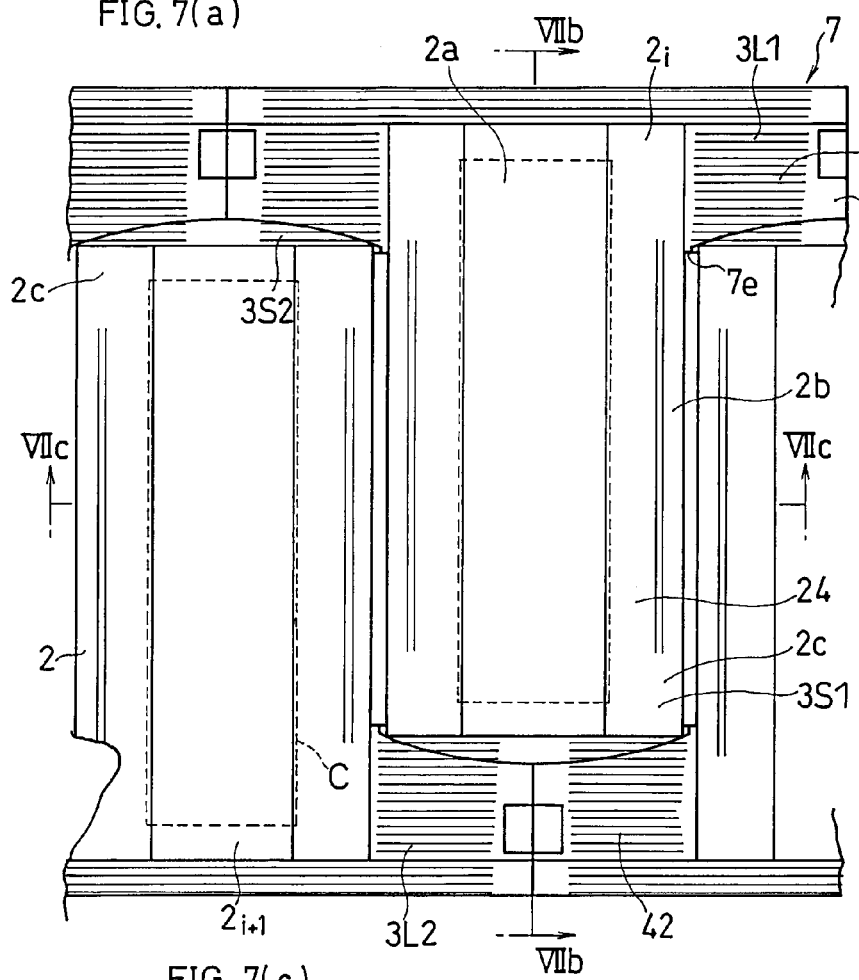
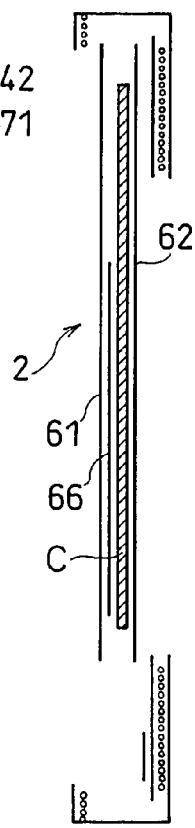
FIG. 7(a)
FIG. 7(b)
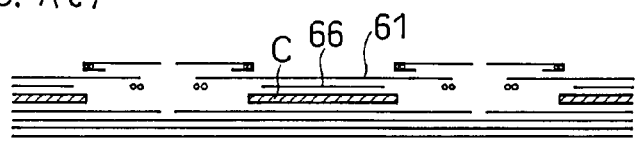
FIG. 7(c)

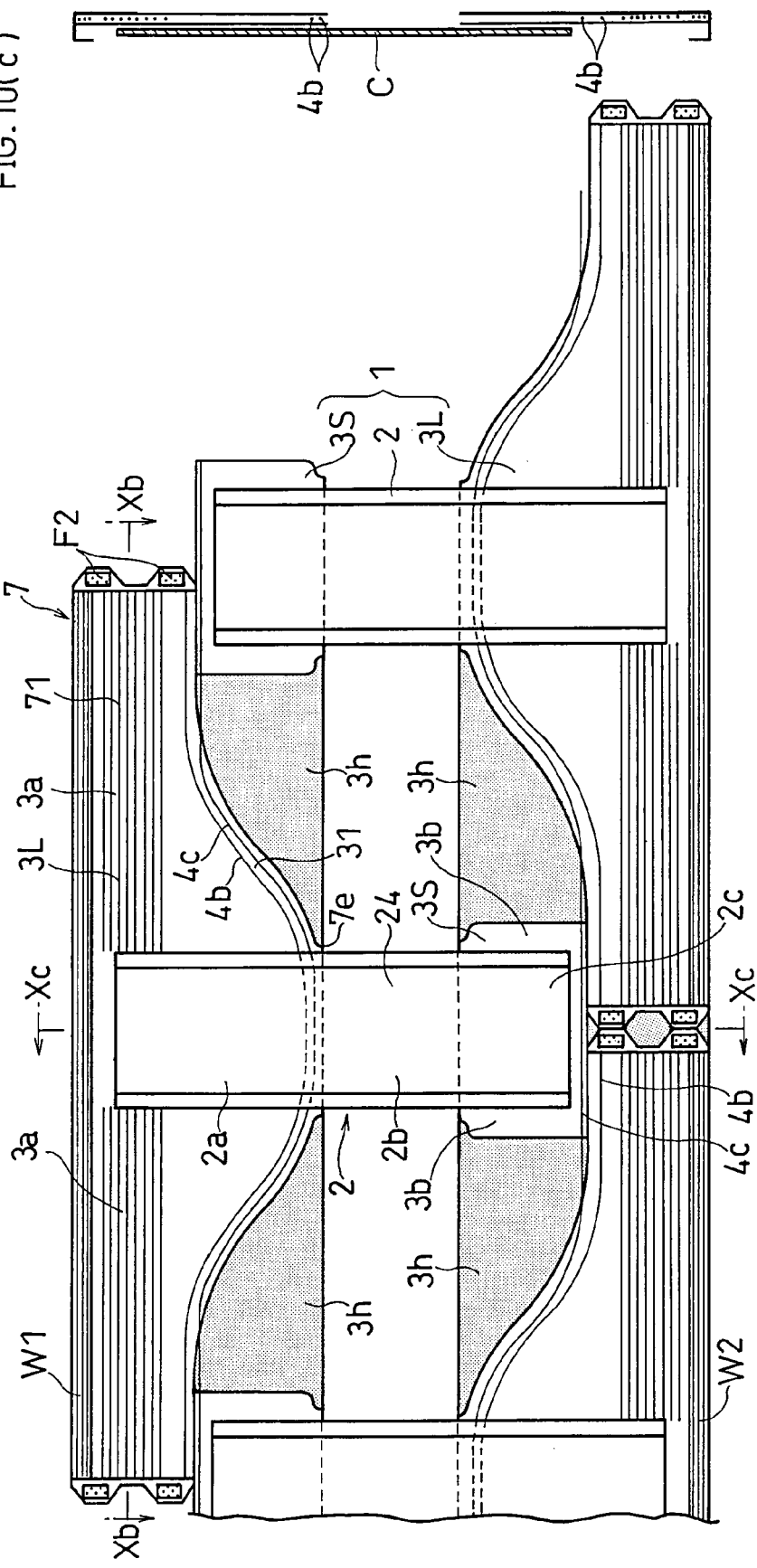

METHOD FOR PRODUCING DISPOSABLE WORN ARTICLE

TECHNICAL FIELD

The present invention relates to a method for producing a disposable worn article.

BACKGROUND ART

Typically, disposable diapers and pants are narrower in portions that cover the crotch of the wearer as compared with other portions that are wound around the waist of the wearer. In order to form narrow portions, the whole cloth web needs to be trimmed substantially. The trimmed portions are discarded, thus wasting the material, which increases the cost and is also not desirable in view of the environmental conservation. For example, the production method of the first patent document below is a method for reducing the portion of the web to be discarded.

First Patent Document: Japanese Laid-Open Patent Publication No. 2003-102777 (ABSTRACT)

DISCLOSURE OF THE INVENTION

However, in a diaper produced by this production method, the width of the core portion covering the crotch is inevitably about one half of the length of the torso portion around the torso. With such a diaper, the fit of the crotch cannot be adjusted without adjusting the ratio of the width of the core portion with respect to the length of the torso portion. Thus, the fit of the crotch is poor. Although opposite ends of the core portion may be cut off in order to improve the fit, it will increase the portion of the web to be discarded.

Therefore, it is an object of the present invention to provide a method for producing a diaper and pants, in which the portion of the web to be discarded can be made as small as possible while improving the fit of the crotch.

It is another object of the present invention to provide a method for producing a worn article, with which the production is easy and the productivity can be improved.

A production method of the present invention is a method for producing a disposable worn article including a front portion and a back portion that fit to a torso of a wearer, and a crotch portion placed between the front portion and the back portion and covering a crotch of the wearer, the method including: a step of carrying a combined member including a strip material in which portions to be the back portions are continuous with one another in a flow direction, and a plurality of protruding portions to be the crotch portions and the front portions, the protruding portions being connected to the strip material, wherein the protruding portions are each protruding from one side edge of the strip material and are spaced apart from one another in the flow direction; a folding step of continuously folding the combined member by bending the combined member at a portion of the protruding portion that is to be the crotch portion; and a step of cutting (severing) the strip material between the protruding portions so as to cut (sever) the folded combined member into individual worn articles, wherein the folding step is performed by raising at least a portion of the strip material and laying the raised strip material on a distal portion of the protruding portion while holding the distal portion that is to be the front portion.

In the present production method, the combined member is folded before being cut into individual worn articles, whereby it is not necessary to fold the crotch portion of individual worn articles, thus facilitating the production. Moreover, the production can be done with relatively simple facilities, and it is therefore possible to reduce the production cost. The combined member is folded while holding a portion of the combined member, thus facilitating the folding process.

In the present production method, the combined member may be placed on the holding means in the folding step so that the distal portion of the combined member faces the suction plane of holding means such as a pad. In such a case, if the distal portion of the protruding portion is air-permeable, the distal portion may be held by air suction and a portion of the strip material that is laid on the distal portion may be held on the skin surface side of the distal portion by an air flowing through the distal portion in the folding step.

In such a case, it is easy to hold the strip material to be the back portion in a folded state while carrying the strip material, and it is possible to eliminate the need for a separate member for holding the strip material.

The folded combined member may be placed on the holding means so that the strip material faces the suction plane of the holding means such as a pad downstream of the folding step. In such a case, if the strip material is air-permeable, the distal portion may be sucked and held via the strip material. Specifically, the strip material of the folded combined member may be held by air suction, and a portion of the distal portion laid on the strip material may be held on the skin surface side of the strip material by an air flowing through the strip material.

In the present production method, it is preferred that in the step of cutting the combined member, the combined member is cut while a bent portion of the protruding portion is held by a holding member.

In such a case, when cutting the strip material, the folded portion of the protruding portion is suppressed from rising, and the combined member is held at an appropriate position, thereby facilitating the cutting of the combined member and improving the precision of the cutting.

The holding member may be any type of member as long as it is capable of holding the bent portion, and may be a belt or a roller, for example.

Another production method of the present invention is a method for producing a disposable worn article including a core portion that covers a crotch of a wearer and a torso portion that fits to a torso of the wearer, with the torso portion including a back portion and a front portion whose length in an around-the-torso direction is shorter than that of the back portion, and with the core portion being placed so as to bridge (extend) between the back portion and the front portion, the method including: a step of carrying a first web including a portion to be an upper side of a waist portion of a first back portion and a second web including a portion to be an upper side of a waist portion of a second back portion in a longitudinal direction of the webs while being parallel to each other and spaced apart from each other; a step of forming a combined member by placing a plurality of core portions so as to bridge (extend) between the first web and the second web while being spaced apart from each other in the longitudinal direction and attaching the core portions to the first web and the second web; and a step of cutting the combined member so as to divide the combined member in a web width direction into a first group including a portion of the first web to be the first back portion and a portion of the second web to be a first front portion attached to the first back portion when worn, and a second group including a portion of the second web to be the second back portion and a portion of the first web to be a second front portion attached to the second back portion when worn, and so that the first and second groups each include the core portions.

In the present invention, the back portion is a portion that covers at least a portion of the back surface of the torso portion of the wearer, whereas the front portion is a portion that covers at least a portion of the front surface of the torso portion of the wearer.

According to the present production method, the combined member is cut in the width direction of the web so as to divide the combined member into pieces, thus forming the back portion and the front portion. Thus, the cut-off line becomes the lower end of the hip portion of the back portion and the upper end (upper side) of the waist portion of the front portion, and a major or substantially entire portion of each web forms the back portion or the front portion of the worn article. Therefore, the unnecessary portion of the web is little, and the portion of the web to be discarded is eliminated or made very little.

Moreover, by employing the present production method, it is possible to adjust the interval between the core portions. Therefore, it is possible to improve the fit in the crotch by adjusting the ratio of the length of the torso portion in the around-the-torso direction with respect to the width of the core portion.

In the present production method, the cut-off line along which to cut the combined member in the step of cutting the combined member is generally represented by a function having a predetermined waveform and a predetermined wavelength, and the combined member is cut so that adjacent core portions belong to the first group and the second group alternately.

In the present production method, the combined member may be cut in the longitudinal direction so that the back portion and front portion are formed for each group by cutting portions of the first and second webs in the width direction of the web.

By this cutting process, the combined member is cut into individual diapers each including the back portion, the front portion and the core portion. The front portion may be formed in a shape protruding in the width direction (the core portion-to-core portion direction) to thereby provide a generally H-shaped diaper, or the front portion may be formed with a length equal to the width of the core portion to thereby provide a generally T-shaped diaper. Separate wing portions may be attached to the distal portion or the front portion of the core portion after the web is cut so that a final product is generally H-shaped.

The worn article produced by the production method of the present invention may be made into a pants-type diaper by detachably attaching the front portion to the back portion by means of touch fasteners or tapes, or may be made into pants by bonding the front portion to the back portion by means of a hot-melt, a heat seal, or the like.

In the step of placing the core portions in the present production method, the core portions may be placed while being shifted from each other in the width direction of the web with respect to the center line running in the longitudinal direction between the first and second webs. In this way, it is possible to place each core portion at an appropriate position between the front portion and the back portion.

The present production method may further include a step of cutting the web of each group into individual worn articles, wherein the worn articles are produced so as to be generally in point symmetry with one another with respect to a point along a center line between the first and second webs extending in a longitudinal direction. The point is at an equal distance from a pair of adjacent core portions.

The present production method may further include a step of cutting the web of each group along a line extending in a width direction that crosses the longitudinal direction into individual worn articles; the step of cutting the combined member is performed by cutting a portion of the first web on which the core portion is not lying along a cut-off line along a portion to be a lower side of the first back portion, thus forming the first back portion and the second front portion in such a manner that a hip portion of the first back portion and the second front portion are adjacent to each other in the longitudinal direction along the cut-off line of the first web and a waist portion of the first back portion and the second front portion are adjacent to each other in the width direction along the cut-off line of the first web, and by cutting a portion of the second web on which the core portion is not lying along a cut-off line along a portion to be a lower side of the second back portion, thus forming the second back portion and the first front portion in such a manner that a hip portion of the second back portion and the first front portion are adjacent to each other in the longitudinal direction along the cut-off line of the second web and a waist portion of the second back portion and the first front portion are adjacent to each other in the width direction along the cut-off line of the second web.

In the present production method, it is more preferable in view of the productivity to perform the step of placing the core portions before the web is cut into two groups. However, the step may alternatively be performed after the web is cut into two groups or after the web is divided into separate diapers.

In the present production method, the step of placing the core portions may be performed by placing a core portion, which is formed by previously sandwiching a highly absorptive material between two sheets, between the first and second webs. However, the step may alternatively be performed by successively placing a highly absorptive material and a top sheet between the first and second webs.

Still another production method of the present invention is a method for producing a disposable worn article including a front portion and a back portion that fit to a torso of a wearer, and a crotch portion placed between the front portion and the back portion and covering a crotch of the wearer, the method including: a step of carrying a continuous web forming at least a portion of the back portion in a longitudinal direction of the continuous web; a step of forming a combined member by attaching a plurality of core portions forming at least a portion of the crotch portion and the front portion to the continuous web while the core portions are aligned in the longitudinal direction, with at least a portion of the core portion to be the front portion protruding from a side edge of the continuous web, and with the core portions being spaced apart from each other in the longitudinal direction; a first folding step of continuously folding the combined member by bending the combined member so that the continuous web is laid on a distal portion of the core portion protruding from the side edge of the continuous web; and a step of cutting the continuous web between the core portions so as to cut the continuous web into generally T-shaped individual worn articles.

With the present production method, it is no longer necessary that the core portions are positionally shifted from one another in the width direction of the web, and it is no longer necessary to perform the step of cutting the combined member into two groups, whereby it is possible to simplify the method and apparatus and to thereby reduce the production cost.

In the present production method, the first folding step may be performed before or after the step of cutting the web into individual worn articles.

BRIEF DESCRIPTION OF THE DRAWINGS

FIG. 1(a) is a plan view showing a diaper according to a first embodiment of the present invention, FIG. 1(b) is a cross-sectional view of FIG. 1(a) taken along line Ib-Ib, and FIG. 1(c) is a cross-sectional view of FIG. 1(a) taken along line Ic-Ic.

FIG. 2 is a perspective view showing the step of placing an elastic member on a web in a production method according to the first embodiment of the present invention.

FIG. 6(a) is a development view showing a combined member having been cut into individual diapers, FIG. 6(b) is a cross-sectional view of FIG. 6(a) taken along line VIb-VIb, and FIG. 6(c) is a cross-sectional view of FIG. 6(a) taken along line VIc-VIc.

FIG. 7(a) is a development view showing a combined member including diapers of another shape and structure, FIG. 7(b) is a cross-sectional view of FIG. 7(a) taken along line VIIb-VIIb, and FIG. 7(c) is a cross-sectional view of FIG. 7(a) taken alone line VIIc-VIIc.

FIG. 10(a) is a development view of a combined member including diapers of still another shape and structure, FIG. 10(b) is a cross-sectional view of FIG. 10(a) taken along line Xb-Xb, FIG. 10(c) is a cross-sectional view of FIG. 10(a) taken along line Xc-Xc.

DESCRIPTION OF THE REFERENCE NUMERALS

Figure 3A:
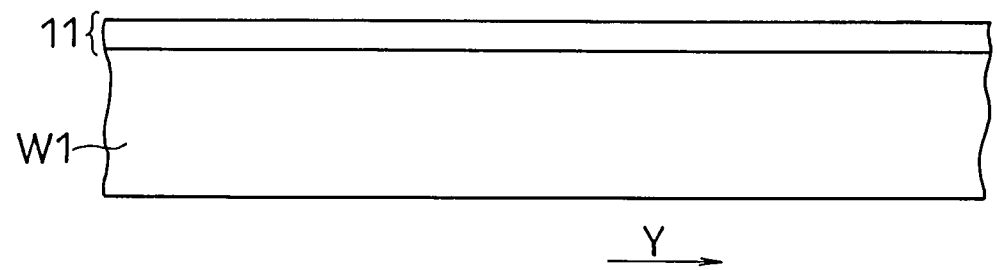
FIG. 3(a) is a plan view showing webs with side edge portions folded back.

1: Diaper
2: Core portion
24: Protruding portion
2b: Crotch portion
2c: Distal portion
3: Torso portion
3L: Back portion
3L1: First back portion
3L2: Second back portion
3S: Front portion
3S1: First front portion
3S2: Second front portion
31e: Lower end of hip portion of back portion
32: Lower end of front portion
7: Combined member
71: Strip material
7e: Side edge
84: Belt
G1: First group
G2: Second group
CL: Center line
W1: First web
W2: Second web
X: Width direction
Y: Longitudinal direction (flow direction)

BEST MODE FOR CARRYING OUT THE INVENTION

First Embodiment

Embodiments of the present invention will now be described with reference to the drawings.

First, an example of a diaper that can be produced by the present production method will now be described before describing the production method of a first embodiment.

In FIG. 1(a), a diaper 1 includes, as an integral part, a core portion 2 and a torso portion 3 having a greater length than the width of the core portion 2. The torso portion 3 includes a back portion 3L that is longer in the around-the-torso direction, and a front portion 3S that is shorter in the around-the-torso direction than the back portion 3L. The core portion 2 is placed so as to bridge (extend) between the back portion 3L and the front portion 3S. The shape of a lower end 31e of a hip portion 31 of the back portion 3L is formed so as to generally coincide with the shape of an upper end 33e of a waist portion 33 of the front portion 3S.

In the diaper 1, the core portion 2 includes, as an integral part, a proximal portion 2a lying on and attached to the back portion 3L, a crotch portion 2b to be placed over the crotch of the wearer, and a distal portion 2c lying on and attached to the front portion 3S. In other words, a portion of the core portion 2 between the proximal portion 2a lying on the back portion 3L and the distal portion 2c lying on the front portion 3S forms the crotch portion 2b, which covers the crotch. The proximal portion 2a and the distal portion 2c of the core portion 2 may form a part of the torso portion. Wing portions 3a and 3a are integrally provided on opposite end portions of the back portion 3L so as to project to the left and to the right with respect to the core portion 2. As the back portion 3L is wound around the torso of the wearer with the wing portions 3a and 3a being attached to the distal portion 2c of the core portion 2 and/or the front portion 3S, the diaper 1 is worn by the wearer. Tab portions 3b and 3b are provided on opposite end portions of the front portion 3S so as to project to the left and to the right with respect to the core portion 2. When wearing the diaper, the attachment of the wing portions 3a and 3a can be made by pulling the back portion 3L while pinching the tab portion 3b.

A first touch fastener F1 (not shown in FIG. 1(a)) is attached to the distal portion 2c of the core portion 2 and/or the front portion 3S, and a second touch fastener F2, which can be touch-fastened with the first touch fastener F1, is attached to the opposite wing portions 3a and 3a of the back portion 3L. The touch fastener F1 may be omitted. In such a case, the outermost sheet of the core portion 2 or the front portion 3S serves the function as the female touch fastener. The touch fastener may be replaced by an adhesive tape and a portion to be bonded to the adhesive tape.

The core portion 2 is provided with an absorbent body C capable of absorbing body fluids discharged from within the body. The core portion 2 may be so long that it reaches a portion of the area of the back portion 3L or the front portion 3S. In the back portion 3L or the front portion 3S, the absorbent body C may be held down by a sheet. The absorbent body C may include a fluff pulp obtained by milling a pulp and/or a super absorbing polymer. The absorbent body C may be an air-laid pulp, or the like.

The absorbent body C may be provided with a plurality of anti-leak walls (so-called "cuffs") 2d for preventing the feces and/or urine from leaking to the outside of the absorbent body C or the diaper. The anti-leak wall 2d may have a three-dimensional configuration. The core portion 2 may be provided with a plurality of leg gathers 2e for preventing the feces and/or urine from leaking out of the diaper. Moreover, a curved elastic member 4b may be provided for forming other leg gathers along the lower end 31e of the hip portion 31 of the back portion 3L.

Elastic members 41 and 43 are placed on the back portion 3L and the front portion 3S so as to form waist gathers for suppressing the slippage between the wearer and the diaper 1. Moreover, elastic members 42 to be fit gathers are placed on the back portion 3L in order to improve the fit of the diaper 1. The elastic members 41 to 43 and 4b may be rubber threads or rubber tapes. The elastic members 41 to 43 and 4b may be made of urethane, or the back portion 3L and/or the front portion 3S may be made from a web having elasticity. In order to prevent the corrugation of the touch fastener or the absorbent body to be described later, the elastic members 41 to 43 and 4b may be partially omitted or may be cut off, for example, so that the elasticity is partially lost.

As shown in FIGS. 1(b) and 1(c), the present diaper includes a plurality of sheet-like members, an absorbent body and elastic members layered together.

As shown in FIGS. 1(a) and 1(b), the core portion 2 includes a liquid-permeable top sheet 61, the absorbent body C, a liquid-impermeable back sheet 62, and an outer sheet 63 layered together. The anti-leak walls 2d are provided on the top sheet 61.

As shown in FIGS. 1(a) and 1(c), the back portion 3L and the front portion 3S include a cover sheet 64 made of nonwoven fabric and the elastic member 42 or 43 layered together. The cover sheet 64 is folded at the waist portion of the back portion. The cover sheet 64 has two layers with the elastic member 42 being interposed therebetween. In the present diaper, it is preferred that a portion of the cover sheet 64 where the elastic members 42 are not provided (a portion corresponding to the proximal portion 2a of the core portion 2) has two layers, but it is not necessary that the cover sheet 64 has two layers.

Next, an example of a method for producing a diaper will be described.

Steps to be described below are performed while carrying two webs W1 and W2 in the longitudinal direction (the flow direction) Y of the webs. The two webs W1 and W2 are carried while being spaced apart from each other in the width direction X of the webs.

As shown in FIG. 2, a first side edge portion 11 of the first web W1 and/or a second side edge portion 21 of the second web are folded back, with elastic members 4 (subsequently to be the elastic members 41 of FIG. 1(a)) being introduced between folded-back portions 11a and 21a and portions 11b and 21b of the web W on which the folded-back portions 11a and 21a are laid, and these members are bonded together by an adhesive. The elastic members 4 (subsequently to be the elastic members 42 and 43 of FIG. 1(a)) are also provided in portions of the first and second webs W1 and W2 other than the side edge portions 11 and 12. Other webs W3 and W4 may be laid on and bonded to these portions. It is not necessary to provide the other webs W3 and W4.

The first and second webs W1 and W2 may be produced by slitting a single web.

The step of placing the elastic members 4 on the first web W1 and/or the second web W2 may be performed so that the elastic members 4 are not placed on portions of the webs W1 and W2 on which the core portion 2 is laid. The intermittent placement of the elastic members 4 can be realized by a method described in Japanese Laid-Open Patent Publication No. 2004-223238, for example.

Thus, as shown in FIG. 3(a), the first and/or second side edge portions 11 and/or 21 are each folded back, with a plurality of elastic members 4 (FIG. 1) being placed therein along the longitudinal direction (the flow direction) Y of the web W. The adhesive may be a hot-melt. The first side edge portion 11 and the second side edge portion 21 may be folded back at the same time, or in different steps. Note that the elastic members 4 (FIG. 1) are not shown in FIGS. 3 to 5.

Figure 3B:
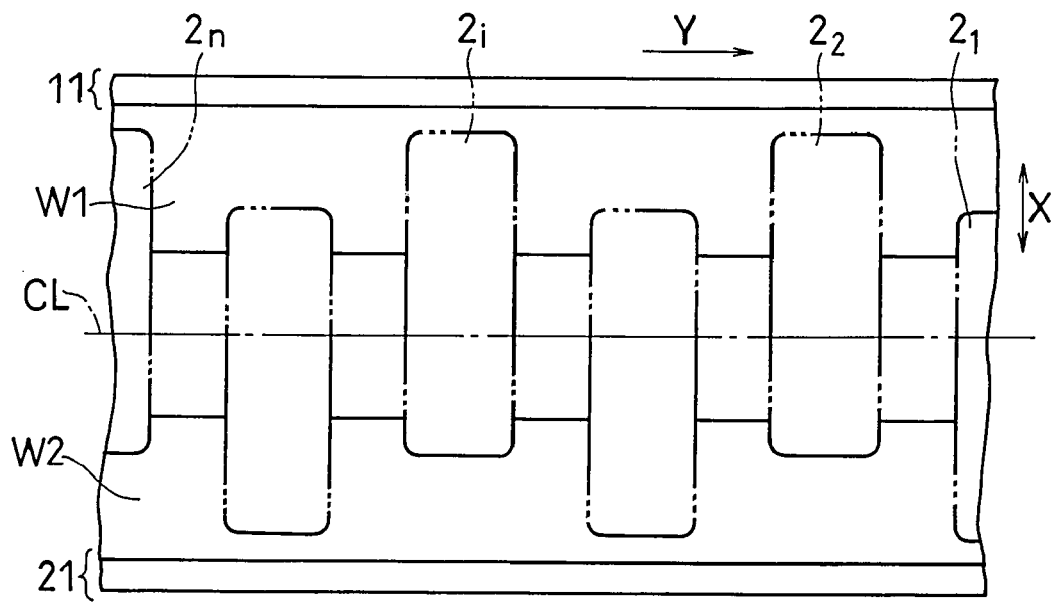
FIG. 3(b) is a plan view showing the webs with core portions placed thereon.

Then, as shown in FIG. 3(b), a large number of core portions $2_i$ are placed on and bonded to the surface of the two webs W1 and W2 to be the inner side when worn so that the core portions $2_i$ are spaced apart from each other in the longitudinal direction Y of the web and so that each of the core portions $2_i$ bridges (extends) between the first and second webs W1 and W2, thus obtaining a combined member. The core portions $2_i$ are placed in the width direction X of the web. In this process, a large number of cores $2_1$ to $2_n$ may be placed so as to be staggered from one another in the width direction X of the web with respect to the center line CL along the longitudinal direction Y of the first and second webs W1 and W2. When placing the core portions $2_i$, the pre-produced core portions $2_i$ may be placed while being turned by 90°. Where the core portions $2_i$ are placed while being turned by 90°, the interval between the core portions $2_i$ may be reduced or increased simultaneously with, or after, the turning.

The pitch of the core portions $2_i$ may be constant. Note that in FIGS. 3 to 5, the core portions $2_i$ are drawn by two-dot chain lines so that they are better distinguished from other members.

Figure 5A:
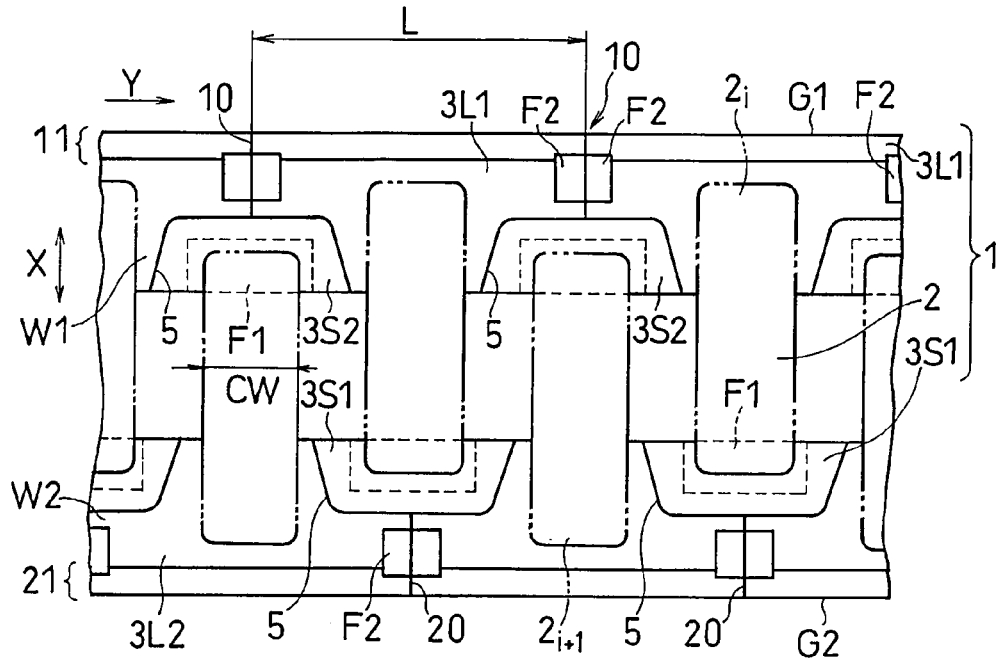
FIG. 5(a) is a development view showing a combined member having been cut into individual diapers.
Figure 5B:
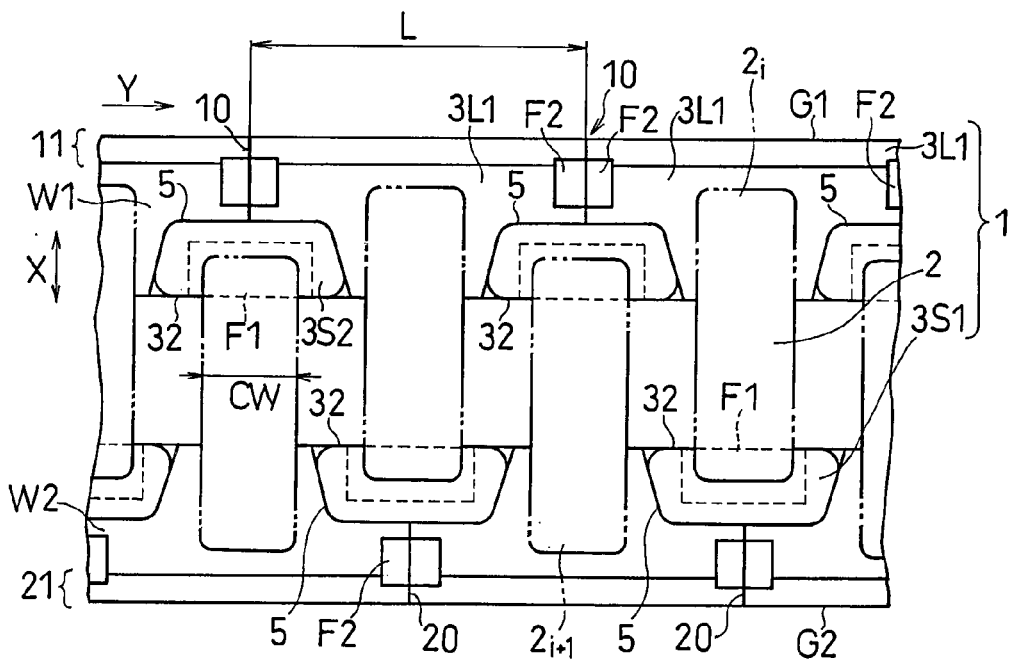
FIG. 5(b) is a development view showing a combined member having been trimmed.

As shown in FIGS. 5(a) and 5(b), the core portions $2_i$ may be placed so that the width L (the length of the back portion) of the diaper is about twice the interval (pitch) of the core portions $2_i$. The width L of the diaper is preferably about 2 to about 11 times the width CW of the core portion $2_i$, and more preferably about 8 times or less of the width CW of the core portion $2_i$.

The core portion $2_i$ may be detachably attached to the first web W1 and/or the second web W2 by a touch fastener, an adhesive tape, or the like. Then, it is possible to produce a worn article with which the core portion can be detached from the torso portion or replaced by a new one after use. In such a case, only the back portion side of the core portion $2_i$, only the front portion side thereof, or both of them, may be detachably attached to the webs W1 and W2.

Figure 4A:
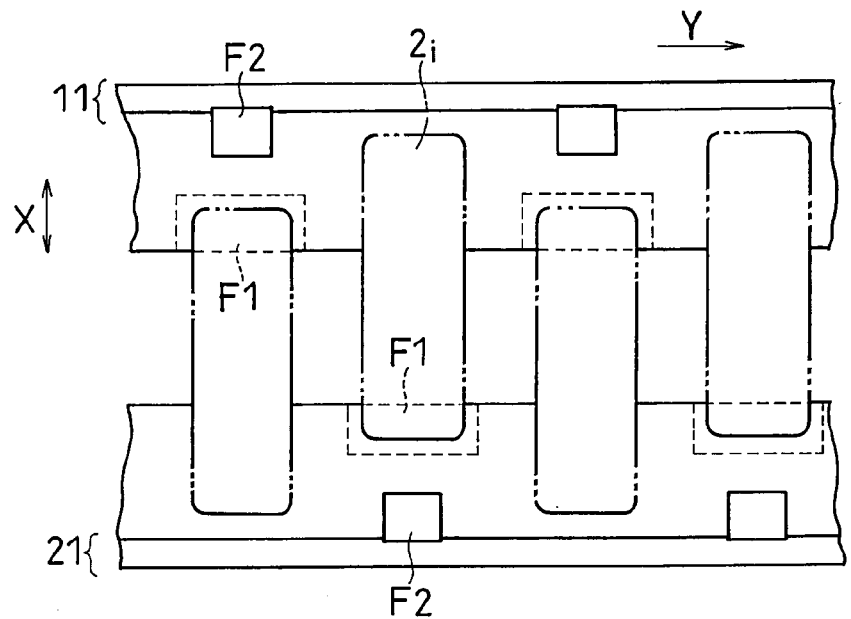
FIG. 4(a) is a plan view showing a combined member with touch fasteners attached thereto.

As shown in FIG. 4(a), the first and second touch fasteners F1 and F2 are placed in (bonded to) predetermined positions of the webs W1 and W2. The touch fasteners F1 and F2 may be bonded in advance to the webs W1 and W2 before the folding step of FIG. 2. Moreover, the second touch fastener F2 may be placed on the upper surface of the webs W1 and W2 (the surface on which the core portions 2 are placed) after the step of folding back the side edge of the web.

As shown in FIG. 5(a), the second touch fastener F2 may be cut and divided into two when adjacent diapers 1 are cut off each other. This is easier than bonding two pre-cut second touch fasteners F2.

Figure 4B:
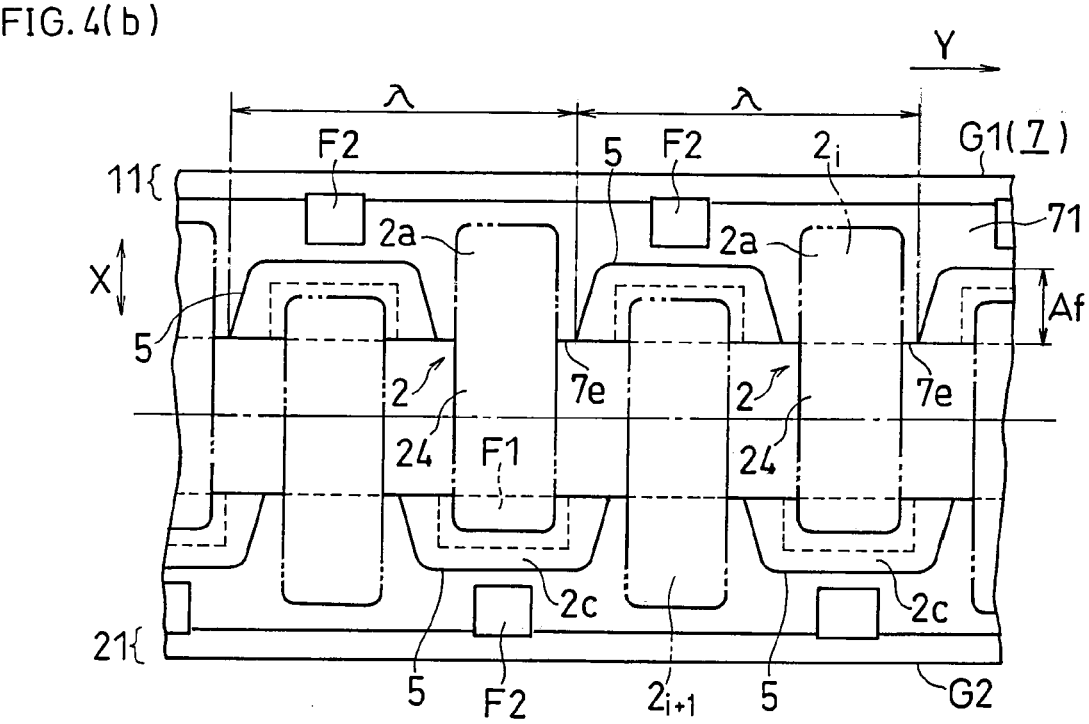
FIG. 4(b) is a plan view showing a combined member having been cut into a first and a second group.

As shown in FIG. 4(b), the webs W1 and W2 are cut along a cut-off line 5 so as to be divided into two in the width direction X of the web, whereby the combined member is cut into a first group G1 and a second group G2. This cutting into groups is preferably performed after the step of folding back the side edge of the web and the step of placing the core portions 2 and the touch fasteners F1 and F2. This is because the productivity will then improve.

As shown in FIG. 5(a), the first group G1 includes a portion of the first web W1 to be a first back portion 3L1 and a portion of the second web W2 to be a first front portion 3S1 that is attached to the first back portion 3L1 upon wearing. The second group G2 includes a portion of the second web W2 to be a second back portion 3L2 and a portion of the first web W1 to be a second front portion 3S2 that is attached to the second back portion 3L2 upon wearing.

As shown in FIG. 4(b), adjacent core portions $2_i$ and $2_{i+1}$ are in many cases belonging to the first group G1 and the second group G2 alternately. The cut-off line 5 along which the first group G1 and the second group G2 are cut off each other may be represented by a periodic function. Specifically, the cut-off line 5 may be represented by a function having a predetermined waveform, amplitude Af and wavelength λ.

As shown in FIG. 5(a), before, simultaneously with or after the cutting into groups, the first and second webs W1 and W2 are cut into adjacent individual diapers 1 along cut-off lines 10 and 20 extending in the width direction X. Thus, the core portions 2 of the diapers 1 belonging to the first group G1 and adjacent to each other sandwich the core portion 2 of a diaper 1 belonging to the second group G2. The second front portion 3S2 belonging to the second group G2 being sandwiched is adjacent to the first back portion 3L1 of the first group G1. The first back portion 3L1 is adjacent to another first back portion 3L1 of the same group.

In the step of cutting the combined member, the portion of the first web W1 on which the core portion 2 is not lying as shown in FIG. 6 is cut along a portion of the first back portion 3L1 to be the lower side (lower end) 31e, whereby the first back portion 3L1 and the second front portion 3S2 are formed so that the hip portion 31 of the first back portion 3L1 and the second front portion 3S2 are adjacent to each other in the longitudinal direction Y along the cutting line (cut-off line) 5, and the waist portion 42 of the first back portion 3L1 and the second front portion 3S2 are adjacent to each other in the width direction X along the cutting line 5. On the other hand, the portion of the second web W2 on which the core portion 2 is not lying is cut along a portion of the second back portion 3L2 to be the lower side (lower end) 31e, whereby the second back portion 3L2 and the first front portion 3S1 are formed so that the hip portion 31 of the second back portion 3L2 and the first front portion 3S1 are adjacent to each other in the longitudinal direction Y along the cutting line 5, and the waist portion 42 of the second back portion 3L2 and the first front portion 3S1 are adjacent to each other in the width direction X along the cutting line 5.

The elastic members 4 (FIG. 1) in portions where the core portions $2_i$ are to be placed may be cut off in advance before the core portions $2_i$ are placed as shown in FIG. 5(a). This is for preventing the core portions $2_i$ from shrinking due to the contraction of the elastic members 4. The elastic members 4 do not have to be introduced in portions where the core portions $2_i$ are placed.

Before the touch fasteners F1 and F2 are attached, if the elastic members 4 (FIG. 1) are present in portions where the touch fasteners F1 and F2 are to be attached, the elastic members 4 in those portions may be cut off in advance. This is for preventing the touch fasteners F1 and F2 from becoming easy to come off due to the contraction of the elastic members 4.

For example, opposite ends of a lower end 32 of the first and second front portions 3S1 and 3S2 may be trimmed as shown in FIG. 5(b). The trimming is done by taking off predetermined portions (hatched portions in FIG. 6(a)) 3h from the webs W1 and W2. The trimming step may be performed simultaneously with, before or after, any step described in the present embodiment.

Another trimming step may be performed so that the crotch portion 2b of the core portion 2 is narrowed as a step to be performed simultaneously with the above-described trimming step or other steps or as a separate step.

With the combined member being cut as described above, two diapers can be arranged in the width direction of the combined member over the width L (the length L of the back portion) of one diaper shown in FIG. 5(a). Thus, the productivity is high.

The touch fasteners F1 and F2 may be replaced by an adhesive tape and a tape for holding the adhesive tape. The female one of the touch fasteners F1 and F2 may be replaced by non-woven fabric.

Thus, there are produced separated individual diapers 1 as shown in FIGS. 6(a) to 6(c). The diapers 1 are produced so that they are generally in point symmetry with one another with respect to the point O along the center line CL that is at an equal distance from a pair of adjacent ones of the core portions 2 (the intersection between the line CL1 between the core portion 2 and the core portion 2 and the center line CL). The back portion and the front portion may be bonded together to thereby produce disposable pants. In FIGS. 6(a) to 6(c), identical or like elements to those shown in FIGS. 1(a) to 1(c) are denoted by like reference numerals and will not be further described below.

Next, a folded configuration and a packaging method for pants-type diapers will be described.

Figure 8A:
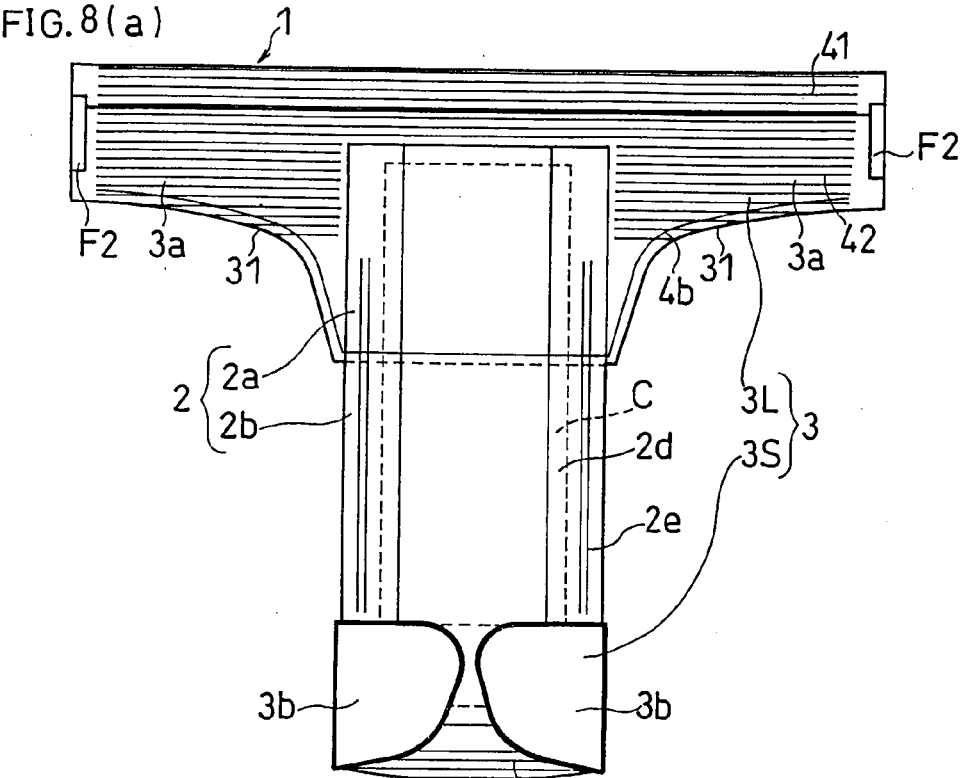
FIGS. 8(a) to 8(c) are plan views of a diaper showing a method for folding a pants-type diaper.
Figure 8B:
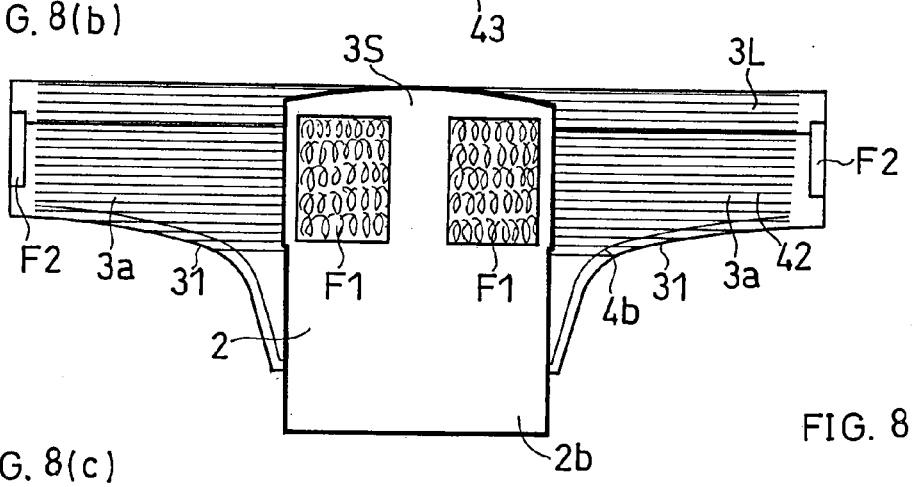
Figure 8C:
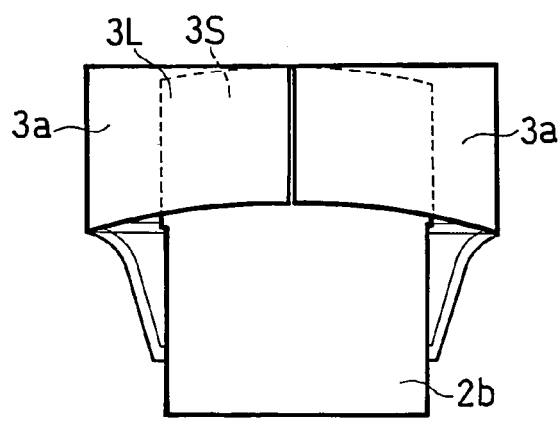

As shown in FIG. 8(a), in a cut-off individual diaper 1, the tab portions 3b and 3b are folded in two so as to lie on the inner surface of the front portion 3S. Then, as shown in FIG. 8(b), the crotch portion 2b of the core portion 2 of the diaper 1 is folded in two so that the front portion 3S lies on the back portion 3L. Then, as shown in FIG. 8(c), the back portion of the diaper 1 is folded in two so that the male touch fasteners F2 on the inner surface of the wing portions 3a of the back portion 3L are attached to the outer surface of the front portion 3S or the touch fasteners F1, thus producing a pants-type diaper. When folding in the wing portions 3a, the wing portions 3a may be folded after the tension thereof has been relieved or the tension thereon may be relieved after the wing portions 3a are folded.

Figure 8D:
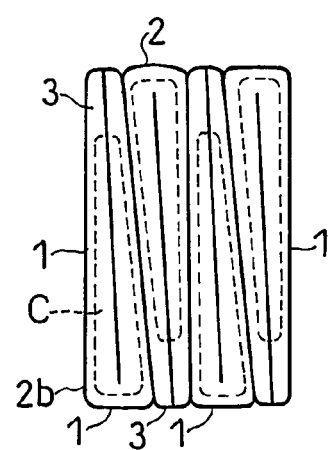
FIG. 8(d) is a side view showing how diapers are packaged together.

At the time of shipping, the present diaper does not have to be in such a form as shown in FIGS. 8(a) and 8(c) where the wing portions 3a of the back portion 3L or the tab portions 3b of the front portion 3S are folded in. When packaging the diapers 1 together, a plurality of diapers may be packaged into a single package so that the torso portions 3 of folded diapers and the bent portions of the crotch portions 2b thereof alternate with each other as shown in FIG. 8(d).

Next, another folded configuration of the diaper will be described.

Figure 9A:
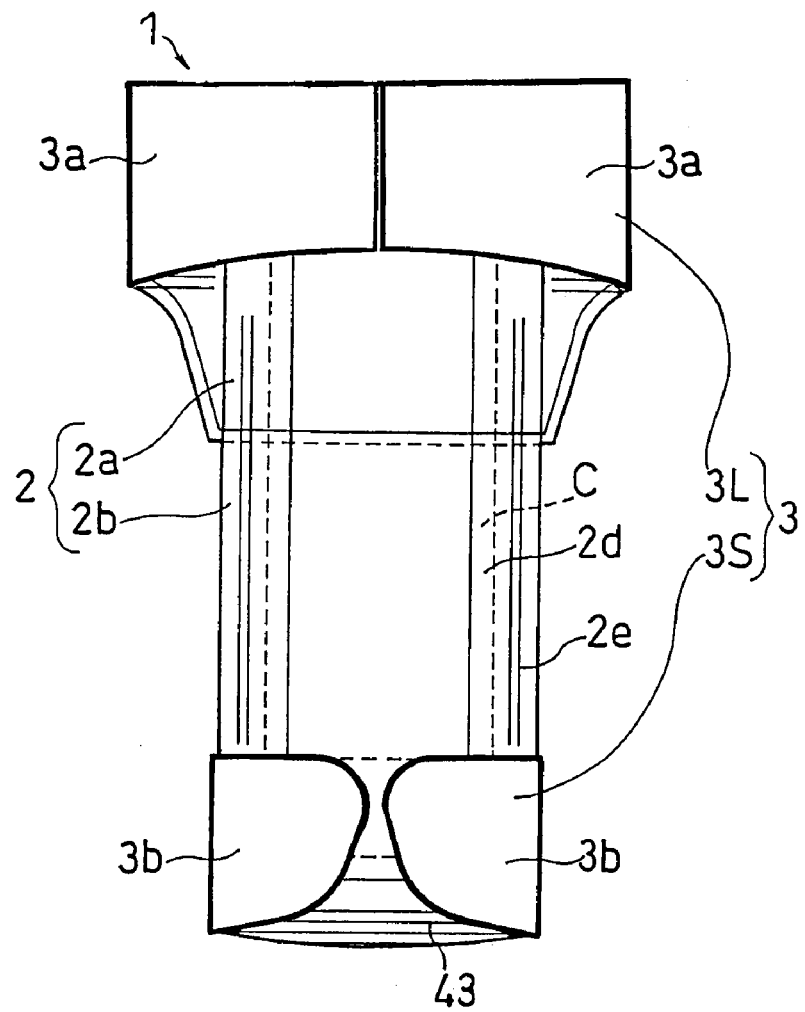
FIGS. 9(a) and 9(b) are plan views of a diaper showing another folding method.
Figure 9B:
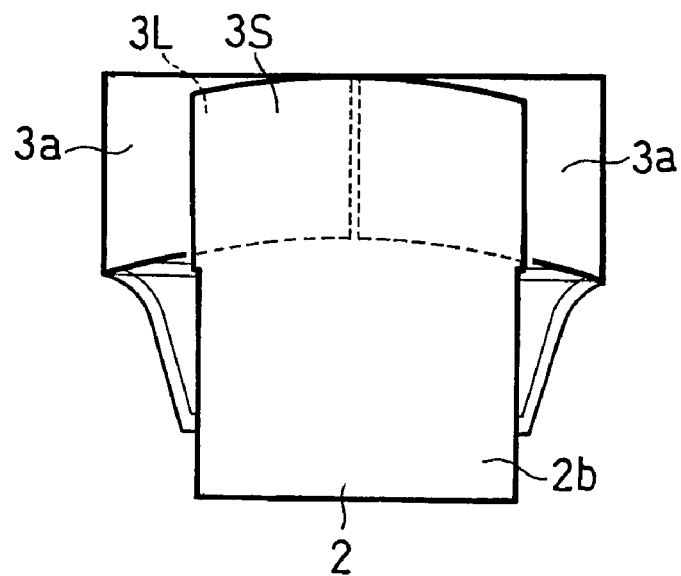

As shown in FIG. 9(a), in a cut-off individual diaper 1, the tab portions 3b and 3b are folded in two so as to lie on the inner surface of the front portion 3S. The wing portions 3a of the back portion 3L are folded in two so that the inner surface of the wing portions 3a of the back portion 3L lies on a central portion of the back portion 3L. Then, as shown in FIG. 9(b), the crotch portions 2b of the core portion 2 of the diaper 1 are folded in two so that the front portion 3S lies on the back portion 3L.

FIG. 7(a) is an exemplary development view of another diaper 1 that can be produced by a method similar to the method described above. What is different from the diaper 1 of FIG. 6(a) will now be described.

In FIG. 7(a), the diaper 1 is generally T-shaped. Specifically, the front portion 3S (3S1, 3S2) does not have tab portions, and is formed with substantially the same width as the core portion 2. Therefore, the interval between two adjacent core portions $2_i$ and $2_{i+1}$ is set to be small. In the present embodiment, the distal portion 2c of the core portion 2 forms a part of the front portion 3S (3S1, 3S2). The elastic members 42 may be omitted in the central portion of the front portion 3S (3S1, 3S2), or the elastic members 42 may be cut into short pieces so that the shrinking force thereof does not act thereupon. A web to be wing portions may be attached to the front portion 3S (3S1, 3S2).

As shown in FIG. 7(b), the outer sheet does not have to be provided on the outer surface side of the back sheet 62. As shown in FIG. 7(c), a transfer sheet 66 is provided between the top sheet 61 and the absorbent body C.

FIG. 10(a) is an exemplary development view of still another diaper 1 that can be produced by a method similar to the method described above. What is different from the diaper 1 of FIG. 6(a) will now be described.

As shown in FIG. 10(a), the present diaper 1 is intended to be a diaper for an adult with a larger around-the-torso dimension, and has wing portions (belt portions) 3a and 3a of the back portion 3L that are longer than those of the diaper 1 of FIG. 5(a), with the tab portions 3b of the front portion 3S being smaller. Therefore, trimmed portions 3h on the left and right of the front portion 3S are as shown by hatching in FIG. 10(a). In the diaper 1, two touch fasteners F2 and F2 are provided in each end portion of the back portion 3L in the around-the-torso direction, with each end portion being partially trimmed.

The diaper 1 includes two elastic members 4b and 4c for forming leg gathers. One elastic member 4c is provided so as to pass through the lower end portion of the hip portion 31 of the back portion 3L of each diaper to be formed on one side and the upper end portion of the front portion 3S of each diaper to be formed on the other side. Thus, the elastic member 4c forms leg gathers in the back portion 3L while forming waist gathers in the front portion 3S.

Second Embodiment

FIGS. 11 to 13 show a method for producing a diaper of the second embodiment. The elastic members are not shown in FIGS. 11 to 13.

Figure 12A:
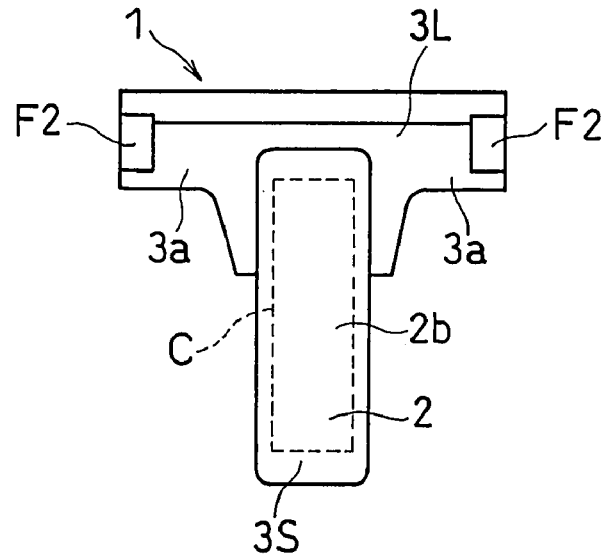
FIG. 12(a) is a plan view showing a diaper according to the second embodiment of the present invention.

The present embodiment will now be described with respect to a generally T-shaped diaper. As shown in FIG. 12(a), the generally T-shaped diaper 1 produced in the present embodiment includes the front portion 3S and the back portion 3L that fit to the torso of the wearer, and the crotch portion 2b provided between the front portion 3S and the back portion 3L so as to cover the crotch of the wearer. The back portion 3L includes the wing portions 3a and 3a projecting to the left and to the right with respect to the core portion 2.

Figure 11A:
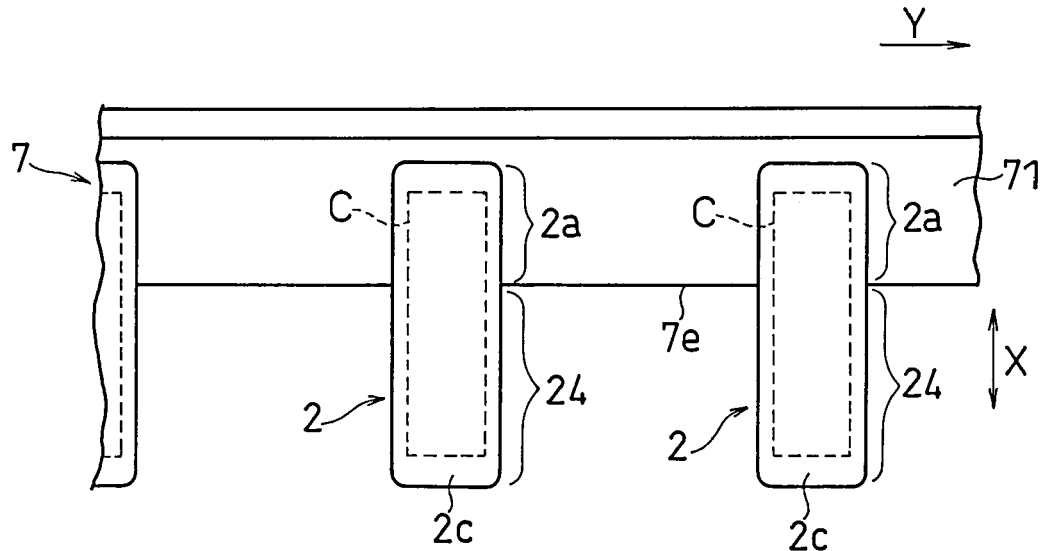
FIGS. 11(a) to 11(c) are plan views showing steps of a production method according to a second embodiment of the present invention.

In order to produce such a generally T-shaped diaper, first, a plurality of core portions 2 are placed on and attached to a continuous strip material 71 while carrying the strip material 71 in the flow direction (longitudinal direction) Y, as shown in FIG. 11(a), to form a generally comb-shaped combined member 7. In this process, the core portions 2 are aligned in the flow direction Y and are spaced apart from one another in the flow direction Y. The longitudinal direction of the core portion 2 is generally perpendicular to the flow direction Y. The core portions 2 may be detachably attached to the strip material 71.

There may be provided a step of placing elastic members on the strip material 71 by a method similar to that of FIG. 2. In such a case, no elastic members may be placed on portions of the strip material 71 on which the core portions 2 are to be laid.

The strip material 71 is a continuous piece where the back portions 3L (FIG. 12(a)), which are to cover the back side of the wearer in produced diapers, are continuous with one another. The core portion 2 includes the proximal portion 2a attached to the strip material 71, and a protruding portion 24 protruding from one side edge 7e of the strip material 71. At least a portion of the proximal portion 2a forms the back portion 3L (FIG. 12(a)) together with the strip material 71 in a produced diaper. The protruding portion 24 forms at least a portion of the front portion 3S and the crotch portion 2b (FIG. 12(a)) in a produced diaper. The core portion 2 includes the absorbent body C having absorptive property. The absorbent body C may be similar to that of the preceding embodiment. The distal portion 2c of the protruding portion 24 of the core portion 2 is air-permeable. The strip material 71 may also be air-permeable.

Figure 11B:
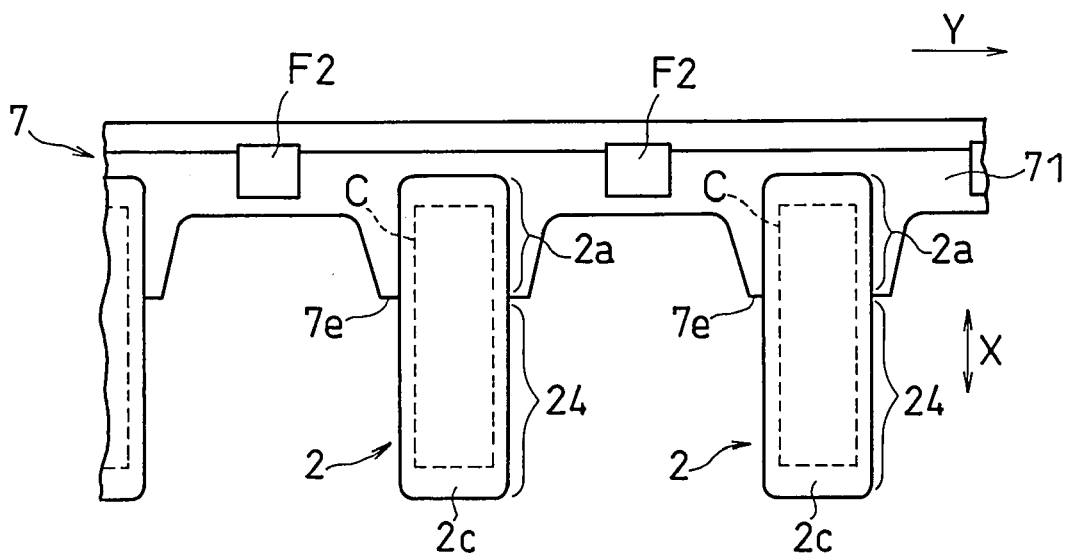

Then, while carrying the combined member 7, the touch fasteners F2 are placed on the strip material 71 between the core portions 2, as shown in FIG. 11(b). Then, the side edge 7e of the strip material 71 is notched in portions between the core portions 2 in order to form leg holes. The first touch fasteners F1 (not shown) may be placed as in the first embodiment. The notching step for forming leg holes may be performed at any time before the folding step to be described later, and may be performed before, after or simultaneously with the step of placing the touch fasteners F1 and F2, or before, after or simultaneously with the step of placing the core portions 2.

Figure 12B:
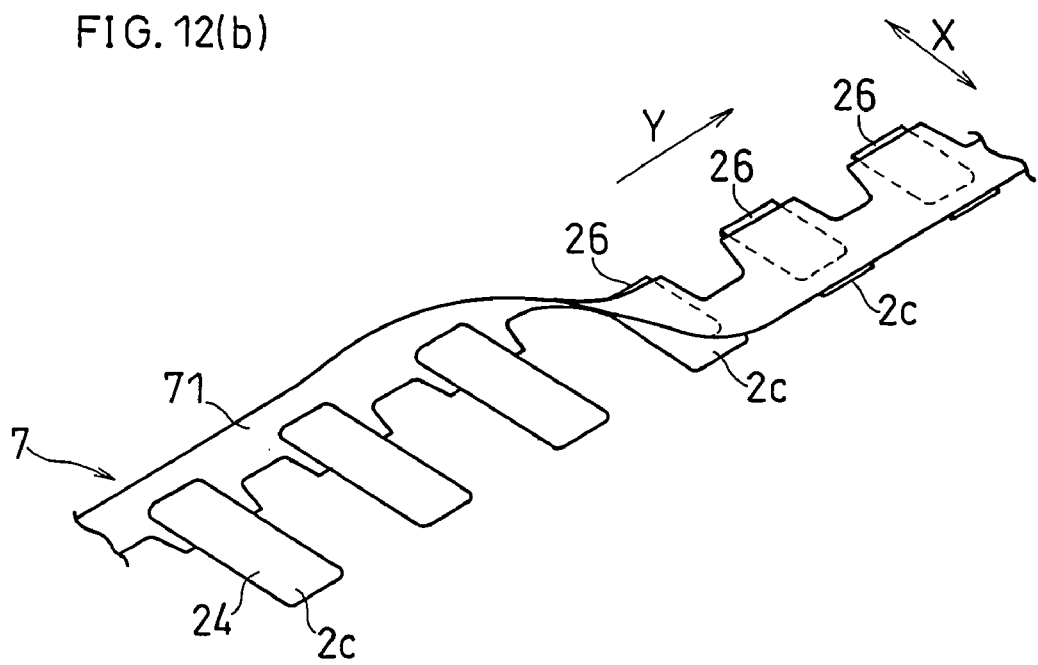
FIG. 12(b) is a perspective view showing a first folding step.

Then, as shown in FIG. 12(b), the combined member 7 is continuously folded at the portion of the protruding portion 24 to be the crotch portion 2b (a generally center portion of the combined member 7 in the width direction X), i.e., a bent portion 26 (the first folding step). The first folding step may be performed after the following cutting step.

In the first folding step, the strip material 71 of the combined member 7 may be raised while the distal portion 2c of the protruding portion 24, for example, is held on a predetermined plane of holding means such as a pad by means of air suction, and the raised strip material 71 may be laid on the distal portion 2c to thereby fold the combined member 7. The folded combined member 7 may be carried while the distal portion 2c side of the combined member 7 is facing the suction plane of the holding means with the distal portion 2c being sucked and held by air. In the folded combined member 7, since the distal portion 2c is air-permeable, the portion of the strip material 71 that is laid on the distal portion 2c can be sucked by the air flowing through the distal portion 2c so as to be sucked onto the skin surface side of the distal portion 2c. In this way, the folded combined member 7 can be carried without raising the overlying strip material 71. The entire protruding portion 24 may be sucked and held by air.

When folding the combined member 7, the web carrying line may be controlled so as to detect a positional displacement between the opposite edge portions and to accordingly control the positional relationship between opposite edge portions so that the edge portion of the waist portion (the upper end of the strip material 71) and the edge portion of the distal portion 2c are laid on each other at a predetermined position. The apparatus for performing the folding process may be a folding apparatus described in WO2004/085300, for example.

The folded combined member 7 may be handed over to another holding means downstream of the first folding step, and the combined member 71 may be carried while the strip material 71 side of the combined member 7 is facing the suction plane of the other holding means with the strip material 71 being sucked and held by air. In such a case, if the strip material 71 is air-permeable, the distal portion 2c laid on the strip material 71 can be sucked and held by the air flowing through the strip material 71.

Figure 11C:
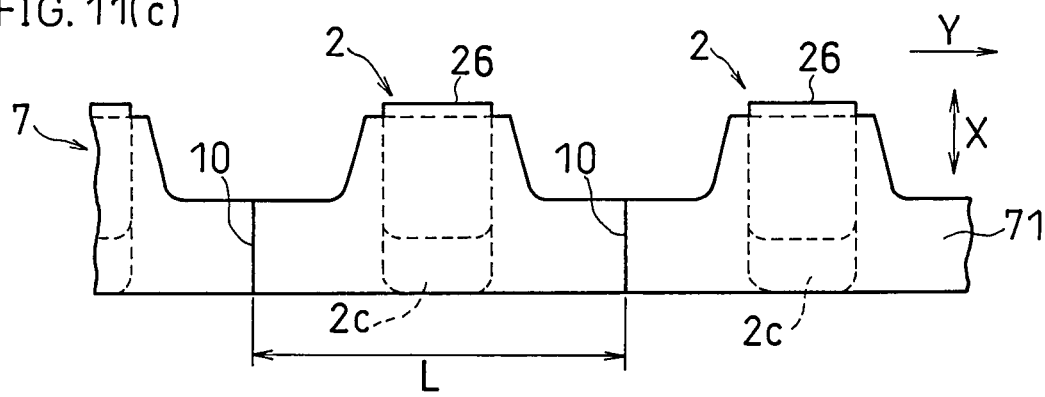

Next, as shown in FIG. 11(c), the strip material 71 is cut, between the protruding portions 24, along the cut-off line 10 extending in the width direction generally perpendicular to the flow direction. The interval L between the cut-off lines 10 is equal to the width of the diaper (the length of the back portion). By this process of cutting along the cut-off line 10, the folded combined member 7 is cut into generally T-shaped individual worn articles.

Figure 13A:
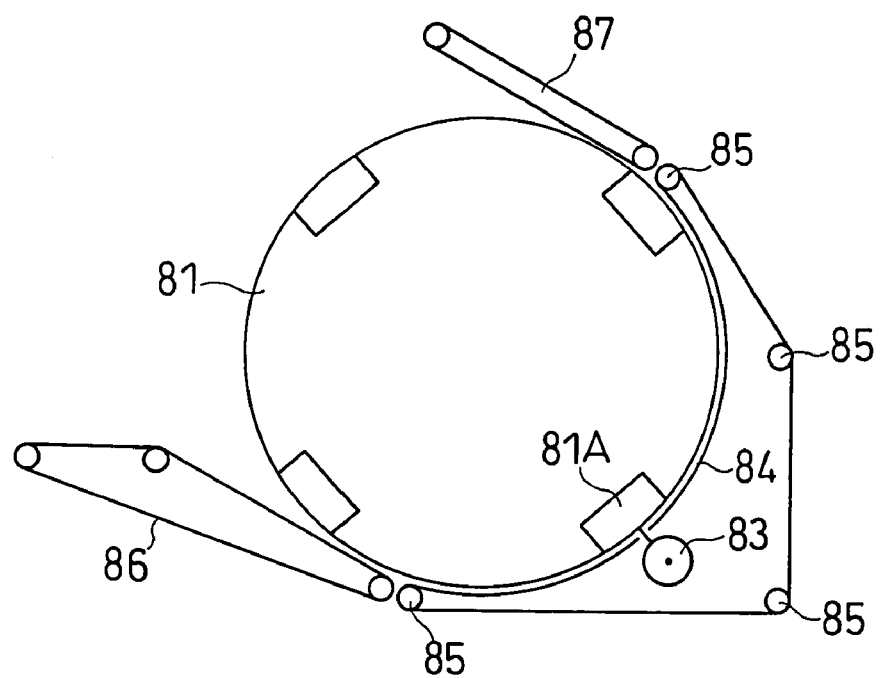
FIG. 13(a) is a schematic side view showing an apparatus for performing the cutting step.

The cutting is performed by using a cutting apparatus of FIG. 13(a), for example.

The cutting apparatus includes an anvil drum 81 having anvils 81A thereon, a cutter roller 83, and a belt 84 for holding a portion of the combined member 7 when cutting the combined member 7. The belt 84 is trained around a plurality of pulleys 85.

Figure 13B:
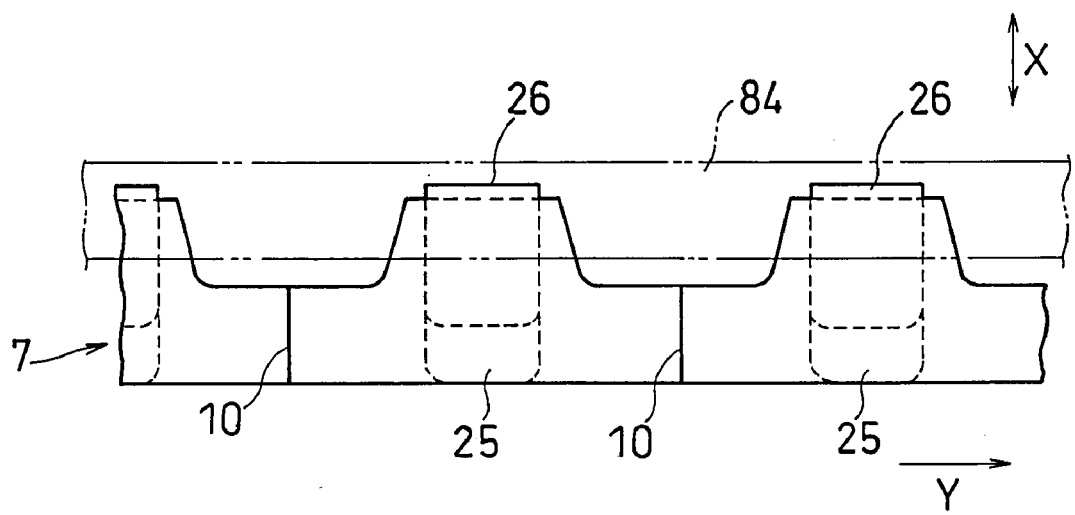
FIG. 13(b) is a plan view showing the cutting step.

The folded combined member 7 is introduced onto the anvil drum 81 by a conveyor 86, and is cut by the cutter roller 83 on the anvil drum 81. In this process, the bent portion 26 of the core portion 2 of the folded combined member 7 and the vicinity thereof are held down by the belt 84 (an example of the holding member; denoted by a two-dot chain line in FIG. 13(b)) as shown in FIG. 13(b). The portion of the combined member to be cut off is not covered by the belt 84. With the holding by the belt 84, the cutting can be done without the bent portion 26 and the vicinity thereof rising inadvertently. The cut-off pieces of the combined member 7 are carried downstream by a conveyor 87.

After the cutting, portions of the back portion 3L protruding to the left and right in each individual diaper are folded in (the second folding step). Specifically, the back portion 3L is folded so that the inner surface (the surface to be in contact with the skin) of the wing portions 3a (FIG. 12(a)) on opposite ends of the back portion 3L faces the outer surface (the surface to be exposed to the outside) of a portion of the core portion 2 closer to the front portion 3S. The second folding step may be performed in a manner similar to that of the first embodiment shown in FIGS. 8(b) to 8(c). A step of changing the attitude of each worn article to an attitude rotated by 90°, a step of adjusting the interval between individual worn articles, and a step of aligning the individual worn articles may be performed before or after the second folding step.

The second folding step may be performed by detachably attaching the core portion 2 to the wing portion 3a of the strip material 71. In this way, the belt portion of the diaper is tentatively engaged with the core portion to thereby provide a pants-type worn article.

While the present embodiment has been described above with respect to a generally T-shaped diaper, the production method of the present embodiment can also be applied to other methods for producing diapers of various shapes as described above in the first embodiment. For example, by pulling the first and second groups G1 and G2 away from each other in the width direction or the up/down direction with the combined member being divided into portions in the width direction X of the web along the cut-off line 5 as shown in FIG. 4(b), it is possible to form two generally comb-shaped combined members 7 each having the strip material 71 and the protruding portion 24 as in the present embodiment. A folding step similar to that of the present embodiment can be performed on the two combined members. The combined member of FIG. 7(a) or 10(a) can similarly be divided into two generally comb-shaped combined members 7, and the production method of the present embodiment can also be applied thereto. One group of FIGS. 4(b), 7(a) and 10(a) is assigned like reference numerals to those used in FIGS. 11(a) to 11(c), and will not be further described below.

INDUSTRIAL APPLICABILITY

The present invention is applicable to disposable diapers and pants.

The invention claimed is:

1. A method for producing a disposable worn article including a core portion that covers a crotch of a wearer and a torso portion that fits to a torso of the wearer, with the torso portion including a back portion and a front portion whose length in an around-the-torso direction is smaller than that of the back portion, and with the core portion being placed so as to bridge between the back portion and the front portion, the method comprising:
   a step of carrying a first web having a first outer side edge portion, which is extending in a longitudinal direction of a continuous web, to be an upper side of a waist portion of a first back portion and a second web having a second outer side edge portion, which is extending in the longitudinal direction of the continuous web, to be an upper side of a waist portion of a second back portion in a longitudinal direction of the webs while being parallel to each other and spaced apart from each other;
   a step of forming a combined member by placing a plurality of core portions so as to bridge between the first web and the second web while being spaced apart from each other in the longitudinal direction and attaching the core portions to the first web and the second web; and
   a step of cutting the combined member, along a line extending in the longitudinal direction, into a first group and a second group so as to divide the combined member in a web width direction into the first group including a portion of the first web to be the first back portion and a portion of the second web to be a first front portion and the second group including a portion of the second web to be the second back portion and a portion of the first web to be a second front portion and so that the first and second groups each include the core portions and so that the first outer side edge portion of the first web is in the first group while outside the second group and the second outer side edge portion of the second web is in the second group while outside the first group.

2. A method for producing a disposable worn article according to claim 1, further comprising a step of cutting the web of each group into individual worn articles,
   wherein the worn articles are produced so as to be generally in point symmetry with one another with respect to a point along a center line between the first and second webs extending in a longitudinal direction, the point being at an equal distance from a pair of adjacent core portions.

3. A method for producing a disposable worn article according to claim 1, further comprising a step of cutting the web of each group along a line extending in a width direction that crosses the longitudinal direction into individual worn articles;

the step of cutting the combined member is performed by cutting a portion of the first web on which the core portion is not lying along a cut-off line along a portion to be a lower side of the first back portion, thus forming the first back portion and the second front portion in such a manner that a hip portion of the first back portion and the second front portion are adjacent to each other in the longitudinal direction along the cut-off line of the first web and a waist portion of the first back portion and the second front portion are adjacent to each other in the width direction along the cut-off line of the first web, and by cutting a portion of the second web on which the core portion is not lying along a cut-off line along a portion to be a lower side of the second back portion, thus forming the second back portion and the first front portion in such a manner that a hip portion of the second back portion and the first front portion are adjacent to each other in the longitudinal direction along the cut-off line of the second web and a waist portion of the second back portion and the first front portion are adjacent to each other in the width direction along the cut-off line of the second web.

4. A method for producing a disposable worn article according to claim 1, further comprising:

a step of cutting the web of each group into individual worn articles;

a step of folding the core portion of each of the cut-off individual worn articles so that the front portion is laid on the back portion; and a step of folding the back portion so that inner surfaces of wing portions on opposite sides of the back portion face an outer surface of the front portion.

5. A method for producing a disposable worn article according to claim 4, further comprising a step of bonding, or detachably attaching, the outer surface of the front portion to the inner surfaces of the wing portions on opposite sides of the back portion, thereby providing a pants-type worn article.

6. A method for producing a disposable worn article according to claim 1, further comprising:

a step of cutting the web of each group into individual worn articles;

a step of folding each of wing portions on opposite sides of the back portion in two so that an inner surface of each wing portion of the back portion faces an inner surface of a central portion of the back portion; and a step of folding the core portion in two so that the front portion of the cut-off individual worn article is laid on the back portion.

\* \* \* \* \*